United States Patent [19]

Kyle et al.

[11] Patent Number: 5,567,732

[45] Date of Patent: Oct. 22, 1996

[54] EICOSAPENTAENOIC ACID-CONTAINING OIL AND METHODS FOR ITS PRODUCTION

[75] Inventors: David J. Kyle; Raymond Gladue, both of Catonsville, Md.

[73] Assignee: Martek Biosciences Corporation, Columbia, Md.

[21] Appl. No.: 934,485

[22] PCT Filed: Mar. 20, 1991

[86] PCT No.: PCT/US91/02052

§ 371 Date: Sep. 11, 1992

§ 102(e) Date: Sep. 11, 1992

Related U.S. Application Data

[63] Continuation-in-part of Ser. No. 496,572, Mar. 21, 1990, Pat. No. 5,244,921.

[51] Int. Cl.$^6$ .................................................. A61K 31/20
[52] U.S. Cl. ......................... 514/560; 514/573; 435/134
[58] Field of Search ............................ 435/134; 514/560, 514/573

[56] References Cited

U.S. PATENT DOCUMENTS

| | | | |
|---|---|---|---|
| 2,725,677 | 12/1955 | Myers | 47/58 |
| 4,615,839 | 10/1986 | Seto et al. | 260/412 |
| 4,670,285 | 6/1987 | Clandinin et al. | 426/602 |
| 4,831,022 | 5/1989 | Hijiya et al. | 514/58 |

FOREIGN PATENT DOCUMENTS

| | | |
|---|---|---|
| 0277747 | 6/1988 | European Pat. Off. |
| 59-046225 | 3/1984 | Japan |
| 8900606 | 1/1989 | WIPO |

OTHER PUBLICATIONS

Biosis 88081708 (1989)—Volkman et al.
Biosis 85008909 (1907)—Vladivostok.
Yazawa et al. *J. Biochem*, 103: 5–7 (1988).
Borowitzka, "Micro–Alga Biotechnology", Cambridge University Press (1988).
Miller et al., *Lipids*, 24:998–1003 (1985).
Stauber et al., *Water Research*, 23(7): 907–911, 1989.
Behrens, et al. "Novel Microbial Products for Medicine and Agriculture", Society for Industrial Microbiology (1989).
Hoeksema et al., "An EPA–Containing Oil From Microalgae In Culture" paper presented at Int'l Conference in St. Johns, Canada Jul. 31–Aug. 2, 1988.
Anderson, *Biochemica et Biophysica Acta*, 528:77–78 (1978).
Li et al., *Br. Phycol. J.* 22: 375–382 (1980).

*Primary Examiner*—Zohreh Fay
*Attorney, Agent, or Firm*—Banner & Allegretti, Ltd.

[57] ABSTRACT

This invention describes a process for producing single cell edible oils containing eicosapentaenoic acid (EPA) from heterotrophic diatoms. The diatoms are cultivated in a fermentor in a nutrient solution containing nitrogen and silicate. Depletion of the nitrogen followed by depletion of the silicate induces the diatoms to synthesize large quantities of edible oil containing EPA which subsequently is recovered. The edible oil, and uses for it, also form parts of this invention as do mutant diatoms capable of producing large quantities of EPA.

5 Claims, 1 Drawing Sheet

EICOSAPENTAENOIC ACID-CONTAINING OIL AND METHODS FOR ITS PRODUCTION

This application is a continuation-in-part of U.S. application Ser. No. 07/496,572, filed Mar. 21, 1990, now U.S. Pat. No. 5,244,921.

BACKGROUND OF THE INVENTION

This invention relates to edible oils containing omega-3-fatty acids, in particular eicosapentaenoic acid (EPA). The invention also relates to methods of producing EPA in commercially viable yields.

Omega-3-fatty acids are known to be beneficial in reducing the incidence of coronary heart disease. The metabolism of omega-3-fatty acids is not understood. Thus, although these acids are known to have beneficial effects, precise clinical dosages and efficacy are not known.

Omega-3-fatty acids, including EPA, have been found in the oils of cold water marine fish. Indeed, this is the primary source of commercially available EPA. It is believed that the omega-3-fatty acids found in fish originate from phytoplankton which are at the base of the marine food chain. The belief is due to the fact that many phytoplankton species are found to contain reserves of oil containing varying amounts of EPA.

Certain marine microorganisms are known to contain EPA. For example, Yazawa et al., *J. Biochem*, 103:5–7 (1988), found 88 strains of gram-negative bacteria which produced EPA. U.S. Pat. No. 4,615,839 (Seto et al.) discloses the cultivation of monocellular green algae in open pools followed by recovery of EPA from those microalgae.

While omega-3-fatty acids are known to have medicinal utility, there are problems associated with their use. Because of their association with fish oils, there is often a fishy odor and unpleasant taste associated with these acids. Additionally, although fish oils do contain EPA, many of these oils cannot be consumed by humans due to the presence of attendant contaminants, such as PCB, as well as a high concentration of oxidation-sensitive polyunsaturated fatty acids, some of which exhibit bioactivities which are different from, and even antagonistic to, EPA. Furthermore, oils from many fish, particularly fish from tropical zone waters, also contain significant quantities of arachidonic acid which exhibits a biological effect antagonistic to EPA. While production of omega-3-fatty acids in microorganisms would eliminate the contaminant problems, no commercially acceptable and economically feasible method of producing large quantities of these acids in microorganisms has been available.

Isotopically labelled EPA would be of great benefit in elucidating the pathway of omega-3-fatty acid metabolism. However, labelled EPA in sufficient quantities to perform such research has not heretofore been obtainable.

Accordingly, it is an object of the present invention to produce EPA in microorganisms by a commercially feasible method to obtain commercially acceptable yields.

Further, it is an object of the present invention to produce isotopically labelled EPA from this cultivation process in amounts sufficient to study omega-3-fatty acid metabolism.

SUMMARY OF THE INVENTION

The present invention relates to the cultivation of microorganisms in a bioreactor, inducing the generation of edible oils containing omega-3-fatty acids in those microorganisms and recovering those oils and/or fatty acids. The invention also is directed to novel oils which contain omega-3-fatty acids but lack the additional polyunsaturated fatty acids associated with fish oils, to diatoms having increased amounts of omega-3-fatty acids as compared to wild type diatoms growing in the wild, and to mutant diatoms. Typically, these oils are further characterized as exhibiting biphasic melting patterns. Furthermore, isotopically labelled omega-3-fatty acids and their production are disclosed.

The present invention provides an economical method of obtaining edible oils having favorable organoleptic characteristics containing EPA without significant amounts of other polyunsaturated fatty acids. Additionally, the method permits cultivation of diatoms to greater cell densities than those typically achieved by prior art processes. The edible oils produced by this method are free of environmental contaminants often found in EPA-containing oils from other sources.

DETAILED DESCRIPTION OF THE BEST MODE OF PRACTICING THE INVENTION

Figure 1:
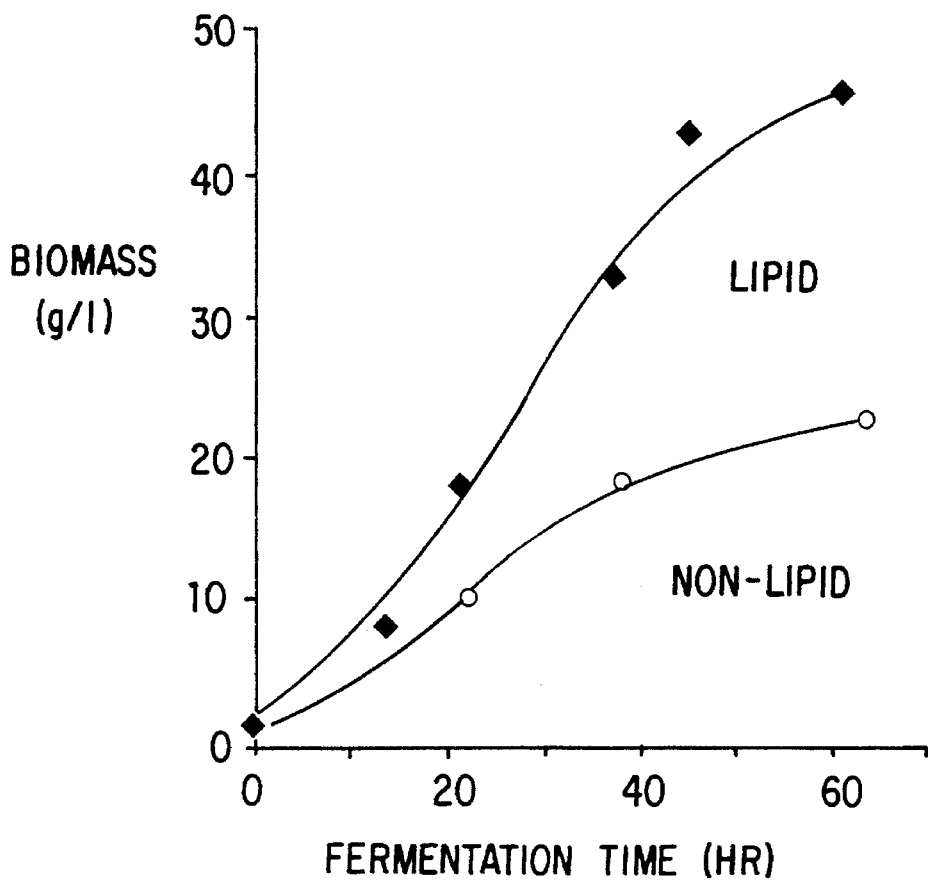
FIG. 1 is a graphic representation of the biomass accumulation in *Nitzschia alba* during its growth and oleogenic phases.
Figure 2:
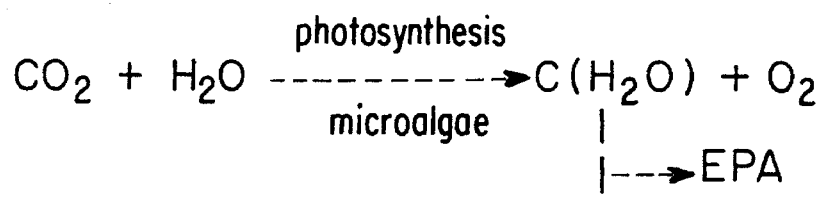
FIG. 2 illustrates the process of labelling EPA with either $^{13}C$ or deuterium.
Figure 2:
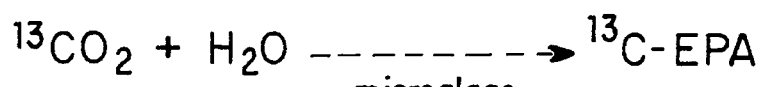
Figure 2:
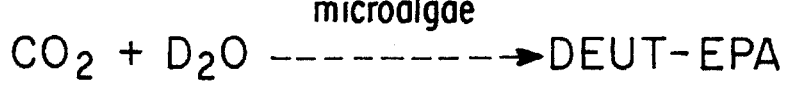

In accordance with the present invention, diatoms capable of producing EPA are cultivated in a fermentor containing a nutrient solution capable of supporting the growth of such microorganisms. In their native environment, heterotrophic diatoms are found growing epiphitically on seaweed. Accordingly, sea water is an acceptable medium for the nutrient solution. The sea water can be either natural, filtered or an artificial mix, each of which can be diluted down to ¼ strength or concentrated to 2×. Micronutrients can be added and may be required, especially if the sea water is an artificial mix. Such micronutrients are known to those of skill in the art and are readily available from commercial suppliers. Additionally, a growth medium specifically designed for growing diatoms is added. A preferred growth medium is presented in Table 1. It is to be understood that variations in this growth medium are well within the ability of skilled workers in this art.

TABLE 1

GROWTH MEDIUM COMPOSITION
Ingredients needed for 2 × 30 L Fermentors and 2 × 350 L Fermentors.

| Recipe | Total 30 L-Batch | 350 L-Batch |
| --- | --- | --- |
| 19 g/L I.O. (Instant Ocean ®) | 570 g | 6.65 Kg |
| 3 g/L NaNO$_3$ | 90 g | 1.05 Kg |
| 0.5 g/L NaH$_2$PO$_4$HH$_2$O | 15 g | 175 g |
| 0.2 g/L Na$_2$SiO$_3$H5H$_2$O | 6 g | 70 g |
| 6 ml/L f/2 TM (trace metals) | 180 ml | 2.2 L |
| 6.0 mg/L H$_3$BO$_3$ | 1.8 g | 21 g |
| 6 mg/L Na$_2$SeO$_3$ | 180 mg | 2.1 g |
| 10 mg/L NaF | 300 mg | 3.5 g |
| 40 mg/L SrCl$_2$H6H$_2$O | 1.2 g | 14 g |
| 150 mg/L KBr | 4.5 g | 52.5 g |
| 0.5 g/L KCl | 15 g | 175 g |
| 2 ml/L B$_6$ TM (trace metals) After Sterilization | 60 ml | 700 ml |

TABLE 1-continued

GROWTH MEDIUM COMPOSITION
Ingredients needed for 2 × 30 L Fermentors and 2 × 350 L Fermentors.

| Recipe | Total | |
|---|---|---|
| | 30 L-Batch | 350 L-Batch |
| 0.1 ml/L of 0.1 mg/ml B$_{12}$ | 3 ml | 35 ml |
| 0.1 ml/L of 0.1 mg/ml Biotin | 3 ml | 35 ml |
| 2 ml/L of 1 mg/ml Thiamine HCl | 60 ml | 700 ml |
| Glucose: | | |
| (1) Start with 80 g/L (40% stock solution) | 6 L | 70 L |
| (2) Add another 40 g/l 1 and 2 (additional 6 liters on day 2) | 3 l | 35 L |
| Silicate: Add 60 ml/liter of 100 g/liter stock solution add additional amounts of stock solution over 48 hours | 1.8 L | 21 L |

Any diatoms capable of producing EPA can be used in the present invention. Moreover, it is preferred to use heterotrophic diatoms. For the purposes of this specification, the term "heterotrophic diatoms" means those diatoms capable of growing in the dark on a particular carbon substrate. Different carbon substrates can be used with different species and such substrates can easily be determined by persons of skill in the art. Preferred genera of diatoms include Nitzschia, Cyclotella and Navicula. Within Nitzschia, the colorless species are especially preferred. In particular, *Nitzschia alba* is especially suitable for use in the present invention. Intended to be utilized in this invention are wild strains, mutants or recombinantly constructed microorganisms which produce increased amounts of EPA when cultured in accordance with the present invention. Suitable diatoms can be isolated from the surfaces of seaweed where they grow epiphitically. A sample of a strain of *Nitzschia alba*, an especially preferred species, has been deposited with the American Type Culture Collection, Rockville, Md., and been assigned Accession No. 40775.

The present invention provides for the culturing of diatoms at a much higher cell density than has heretofore been obtainable. Cell density refers to the amount of biomass present in the fermentator. Typically, cell density accumulations in open pond cultivation of diatoms is from about 0.2–1 grams dry weight/liter. In contrast, by applying the method of the present invention, and cultivating the diatoms in a fermentor, biomass densities of from 40–50 grams dry weight/liter have been obtained. Such a high cell density contributes to the enhanced production of edible oils containing EPA.

Together with sea water, the growth medium hereafter will be referred to as a nutrient solution. The nutrient solution typically includes available nitrogen. By available nitrogen is meant nitrogen in a form suitable for diatom use in the biosynthesis of nitrogen containing molecules. Examples of suitable forms of such nitrogen include sodium nitrate or potassium nitrate. Sodium nitrate is preferred. To obtain an amount of diatom biomass equal to about 50 g/per liter of solution, about 3 to about 4 grams of sodium nitrate per liter of solution should be provided. The nitrate can be included in the initial medium sterilization and need not be added thereafter.

Also added to the medium, after sterilization, is a quantity of diatoms sufficient to inoculate the fermentor. These initial diatoms are referred to herein as the "seed" diatoms. Generally seed diatoms are obtained by culturing diatoms on agar plates and transferring cells from the agar plates to tubes containing 2–5 ml of culture medium. After a period of growth, the cells in the tubes are in turn used to inoculate 50 ml of medium in a 250 ml shake flask. The contents of the inoculated shake flask are used as the seed for a 2 liter fermentor. In production runs it is preferred to use seed culture medium in volumes of from about 5 to 10% of the volume of the fermentor. For example, in a 300 liter fermentor from about 15 to 30 liters of seed culture medium preferably would be added.

As the diatoms are being cultivated they are fed both silicate and carbon. A preferred form of silicate is metasilicate, $Na_2SiO_3$. Metasilicate has both a 5 and a 9 hydrate form. Either form is acceptable for use in the present invention. In a nutrient solution having a typical pH and salinity permitting the growth of diatoms, metasilicates irreversibly form a polymeric precipitate at concentrations in excess of about 250 mg/l. Such precipitates are unacceptable as they make the silicates unavailable for use by the diatoms. This previously unsolved problem is overcome in the present invention where from about 5 to about 7 grams of metasilicate per liter of nutrient solution desirably is added to the fermentor. The undesirable precipitation is avoided by feeding the metasilicate into the fermentor at a controlled rate. The metasilicate can added incrementally in a fed batch mode. Preferably it is added in a continuous gradient feed. A continuous gradient feed is a slower rate of addition than a fed batch mode, as will be understood by those of skill in the art. Those of skill in the art, in possession of this invention, can easily determine without undue experimentation suitable rates of silicate addition.

During the growth phase of the diatoms the ratio of silicate to carbon preferably is kept constant. Therefore, these two nutrients can be fed to the batch together at intervals throughout the cultivation. Using glucose as an example of a carbon source, the ratio of glucose to metasilicate desirably is from about 10 grams to 35 grams of glucose per gram of metasilicate. A particularly preferred ratio is about 20 grams of glucose per gram of metasilicate. Those of skill in the art can easily calculate acceptable ratios using other carbon sources, such as hydrolyzed whey, or starch.

Alternatively, the carbon source can be added batch-wise, i.e. enough carbon source for a complete batch is added at the beginning of the fermentation. If this alternative is chosen, the metasilicate is added slowly to the fermentation, effectively controlling the rate of growth of the diatoms. Typical growth rates will comprise a doubling of the biomass every 4–8 hours.

While any type of fermentor can be used with the present invention, stirred-pot fermentors with conventional Rushton turbine-agitation are a preferred embodiment. Such turbines agitate by rotating a shaft having protruding flat blades for maximum aeration. Preferably the speed of rotation is kept to a speed of less than 250 cm/sec at the tip of the shaft. Maintaining the speed at less than 250 cm/sec reduces the likelihood of shearing, or otherwise damaging, the diatoms. An especially preferred fermentor for large-scale cultivation is an air-lift fermentor. Such fermentors are well known to those of skill in the art and eliminate potential shear damage.

According to the process of the present invention, heterotrophic diatoms are cultivated in fermentors as described above. While phototrophic microorganisms typically produce some EPA when cultivated in, for example, open ponds, it unexpectedly has been found that heterotrophic diatoms can be induced to enter an oleogenic phase wherein they produce a single cell oil containing EPA. FIG. 1 demonstrates the increased production of biomass during oleogenesis. From about 40 to 50% of this biomass can be attributed to oil production. Induction of oleogenesis can be triggered by depriving the microorganism of certain nutrients. In particular, it is known that limiting the availability of nitrogen triggers oleogenesis in many oil producing microbes. Moreover, limiting the availability of silicon to diatoms is known to trigger oleogenesis. Borowitzka, "Micro-Algal Biotechnology", Cambridge University Press (1988). However, in the present invention it has been discovered that the timing of the imposition of a silicon deficiency substantially increases the production of edible oil containing EPA by the diatom.

After about 24 to 48 hours of cultivation, the diatoms have depleted the available nitrogen in the growth medium. At this time, they typically have achieved a biomass density of 20 to 30 g/l which can be measured as the mass of the freeze dried pellet of cells from a known volume of culture. Of course, this time period is somewhat flexible as it depends in part on the amount of nitrogen initially added and on the rate of silicon feed. For several hours after nitrogen depletion occurs, silicate and glucose continue to be fed to the diatoms. While these additional nutrients can be added either continuously or incrementally, it is preferable to add the nutrients incrementally. Generally, the time period of this subsequent silicate feeding will be from about 12 to about 24 hours and is terminated when about 5 g/l of metasilicate, in total, has been added to the culture. The diatoms then enter an oleogenic phase wherein enhanced amounts of edible oils containing EPA are more rapidly synthesized. The oleogenic phase can be continued for varying amounts of time but preferably is from about 12 hours to about 36 hours duration. Preferably the oleogenic phase will be permitted to continue for about 24 hours. During this phase EPA is produced as a single cell oil. For the purposes of this specification, single cell oil means a triglyceride product of a unicellular microorganism. The particular length of time of the oleogenic phase will depend upon the type of microorganism cultivated and the available nutrient supply and can be determined by those of skill in the art. In the case of *Nitzschia alba* the yields begin to decrease if this stage is longer than about 24 to 36 hours. Harvesting to obtain the oil containing EPA can occur immediately following the oleogenic phase.

An oxygen concentration greater than that required by aerobic respiration of the cells enhances diatom growth and EPA synthesis. The elevated level of oxygen is provided by high aeration rates, direct $O_2$ sparging or fermentor pressurization. There is a direct correlation between dissolved oxygen concentration and EPA synthesis because $O_2$ is a substrate for EPA synthesis. At a dissolved oxygen concentration of 30% of air saturation, typical EPA levels in the oil are from about 2 to about 3%. At a dissolved oxygen concentration of 50% of air saturation, the EPA content of the oil increases to about 4–5%.

The cultivation can be carried out at any temperature at which diatoms can be grown. A preferred temperature range is from about 15° C. to about 40° C. A convenient, and economical, temperature to carry out the cultivation is 30° C. Herein lies another advantage of the present invention over, for example, cultivation in open ponds which are subjected to extremes of weather. Temperatures at the lower end of the above range tend to improve the level of EPA with respect to unsaturated fatty acids but such temperatures also decrease the overall productivity rate. The highest productivity rates, as measured by the rate of biomass doubling, occur at about 30° C.

The cultivation can be carried out over a broad pH range. A preferred pH is from about 7.0 to about 8.5. This pH range can be maintained by the addition of concentrated silicate solution at a pH of about 12. If pH adjustment is required above and beyond what the addition of silicate effects, either sodium or potassium hydroxide can be added in an amount effective to adjust the pH.

Also encompassed by this invention are mutant strains of diatoms having increased amounts of EPA, lower amounts of saturated fatty acids or both. Techniques for obtaining mutant strains, such as treating with a mutagen and screening for progeny having the desired characteristics, are known to those of skill in the art. As used herein, "increased" or "lower" means an amount greater or lesser, respectively, than the amount ordinarily found in wild type diatoms.

Diatoms comprising about 40% triglycerides as their biomass are a portion of this invention. Typically, wild type diatoms are found to comprise from about 5 to about 20% triglycerides as their biomass. Because a portion of this invention lies in the recognition that diatoms successfully can be economically cultivated to produce large quantities of single cell oil, the cultivation of such diatoms to obtain any single cell oil is contemplated to be within the scope of this invention. For example, wild type diatoms of the species *Nitzschia alba* typically have less than about 3% EPA and 40–60% of saturated fatty acids. The same species in the present invention typically has from about 3–5% EPA and 50% of saturated fatty acids. This increased percentage of EPA is desirable.

Additionally, the triglycerides of the present invention exhibit a biphasic melting pattern. As diatoms are not animals such an effect is unexpected, as will be appreciated by those of skill in the art. Such a melting pattern is exhibited by dairy fats, such as butter, but has not heretofore been reported in a single cell oil from any other primary producer. Accordingly, single cell oils produced by the method of the present invention containing triglycerides exhibiting a biphasic melting pattern also form a portion of this invention.

A preferred oil produced by the process of this invention has the following fatty acid composition.

| Fatty Acid | 14:0 | 16:0 | 18:1 | 18:2 | 18:3 | 20:4 | 20:5 | Others |
|---|---|---|---|---|---|---|---|---|
| % Composition | 23 | 33 | 33 | 2 | 1 | 1 | 4 | 3 |

As discussed above, the present invention provides a method for reliably and consistently obtaining large quantities of an EPA-containing oil. Typically, in one embodiment of the invention the diatoms are synthesizing at least about 20% of their biomass as edible oil. Because the edible oil is a single cell oil, its recovery is greatly facilitated. After the oleogenic phase, the diatoms can be extracted wet or dry, according to techniques known to those of skill in the art, to produce a complex containing lipids. After extraction, this complex of lipids can be further separated to obtain EPA using known techniques. The preferred dry extraction method uses hexane as the extracting solvent. The cells are first centrifuged, and the cell pellet frozen and lyophilized prior to extraction with hexane. Such an extraction requires little or no physical disruption of the cells. Extraction with the hexane at 40° C. in a volume to mass ratio of hexane to dry biomass of about 4:1 obtains greater than about 95% of the oil within about 0.5 hour. If a wet cell paste rather than dried cells is used, then a mixture of ethanol and hexane is the preferred extraction medium.

The edible oil of the present invention contains fatty acids in addition to EPA. Predominantly, these other lipids are of only three types, palmitic (16:0), oleic (18:1) and myristic (14:0), thereby simplifying the purification process. In contrast, fish oils contain a wide variety of fatty acids in addition to EPA.

Quantities of EPA of sufficient purity and amount to perform research on EPA metabolism can be obtained by the method of the present invention. Accordingly, by including an isotope in the nutrient solution, labelled EPA will be synthesized by the diatoms and can be recovered. If the labels are of the type known as stable isotopes such as deuterium or carbon 13 or radioisotopes such as tritium or carbon 14, the EPA will incorporate those labels and can be used in tracer studies in animals or humans or other research. It is to be understood that in addition to providing a labelled carbon substrate such as $^{13}$C-glucose or $^{14}$C-glucose to a heterotrophic diatom grown in the absence of light sources, $^{13}CO_2$, or $^{14}CO_2$ can be provided to an autotrophic photosynthetic diatom. In both instances $D_2O$ or $^3H_2O$ can be supplied. Autotrophic diatoms also must be exposed to a light source of sufficient intensity to facilitate photosynthesis. Suitable photosynthetic species include those from the genus Cyclotella, Navicula, Phaeodactylum and Monodus. These organisms are preferred for the production of labelled EPA as they are autotrophic and contain higher levels of EPA than *Nitzschia alba*.

The present invention also includes food and feed products, dietary supplements and cosmetics which contain EPA produced by the methods disclosed herein. For example, due to the high protein content and elevated levels of EPA, the EPA-producing microorganisms, taken as a whole cell biomass paste, can be used as feeds for aquaculture, including fish, shellfish and zoo plankton. In addition foods or dietary supplements containing EPA are believed to be effective in reducing coronary disease.

The oil produced by the methods of this invention, and the EPA recovered therefrom, also has beneficial effects, at least in part, in the treatment of skin disorders such as psoriasis. The use of EPA from fish oil has been reported to have a beneficial effect on skin lesions caused by psoriasis. Accordingly, cosmetics containing the single cell oil of this invention or the EPA recovered therefrom are included within the scope of this invention. In particular, skin treatments, lotions or creams containing the single cell oil are contemplated. Such would have an olfactory advantage over fish oils containing EPA and also would not possess the other contaminants found in fish oil.

The present invention having been generally described, reference is had to the following non-limiting specific example.

EXAMPLE

Into a conventional 30 liter stirred tank fermentor (STF) is added the nutrient medium of Table 1, exclusive of the vitamins, glucose and silicate. The fermentor is equipped with a Rushton-type turbine agitator. The STF and the medium are sterilized. After cooling the medium to about 30° C., the vitamins are added, followed by the addition of sufficient amounts of 40% glucose syrup to provide a glucose concentration of about 80 g/l. Concentrated sodium metasilicate pentahydrate (100 g/l) is then added to provide a total silicate concentration of about 200 mg/l. Next, the inoculating amount of culture is added in an amount approximately equal to 5% of the total volume of the fermentor, e.g. 1.5 liters/30 liters. Agitation is commenced with the tip speed set to 85–90 cm/sec and air sparging at 1 VVM started. Over about 16 hours an additional charge of concentrated metasilicate (0.53 liters) is added and the agitation speed increased to 126 cm/sec. Over about the next 24 hours, more concentrated silicate (0.83 liters) is added. Agitation speed again is increased to about 180–185 cm/sec. Over about the next 3 hours an additional 0.15 liters of concentrated metasilicate is added. Thus, the total amount of metasilicate added is about 156 grams or about 1.6 liters of concentrated solution. At about 48 hours additional glucose (about 5 liters) is added, for a total glucose addition of about 4.8 Kg or about 12 liters of 40% glucose syrup. The culture is permitted to grow for an additional 16 hours, maintaining the agitation speed and aeration rate. Then, the fermentor is harvested using a Sharples continuous flow centrifuge producing a biomass density of approximately 45–48 grams dry weight per liter. The resulting pellet, about 20–38% solids, is removed and frozen to about –20° C. A vacuum tray drier is used to remove water from the pellet. The single cell oil pellet then is extracted with hexane. The hexane subsequently is removed by distillation leaving the extracted single cell oil.

We claim:

1. A diatom grown heterotrophically containing a single cell oil comprising triglycerides containing EPA residues.

2. A diatom according to claim 1 comprising about 40% of its biomass as triglycerides.

3. The diatom of claim 2, wherein said triglycerides exhibit a biphasic melting pattern.

4. An edible oil having triglycerides containing EPA, said oil produced by cultivating heterotrophic diatoms in a bioreactor containing a nutrient solution including silicate and available nitrogen, inducing said diatoms to enter an oleogenic phase wherein said diatoms are synthesizing at least about 20% of their biomass as edible oil and recovering said oil.

5. The diatom of claim 3 wherein said triglycerides comprise fatty acids and the fatty acids comprise from about 2 to about 20% EPA.

* * * * *